United States Patent [19]

Wang

[11] Patent Number: 4,680,410

[45] Date of Patent: Jul. 14, 1987

[54] PREPARATION OF N- AND S-1,2-ETHYLENICALLY UNSATURATED ORGANIC COMPOUNDS

[75] Inventor: Pen C. Wang, Midland, Mich.

[73] Assignee: The Dow Chemical Company, Midland, Mich.

[21] Appl. No.: 585,945

[22] Filed: Mar. 2, 1984

[51] Int. Cl.$^4$ .................. C07D 207/12; C07D 263/04; C07D 261/02; C07D 231/04; C07D 239/04; C07D 211/40; C07D 243/04; C07D 223/10

[52] U.S. Cl. .................... 548/231; 548/110; 548/337; 548/406; 548/543; 548/545; 548/211; 548/243; 546/14; 546/243; 544/97; 544/309; 544/315; 540/200; 540/485; 540/526; 564/509; 568/69; 556/407; 556/411; 556/426

[58] Field of Search ............... 548/110, 231, 543, 337, 548/243; 564/205; 540/200, 485; 544/315, 243; 546/121

[56] References Cited

U.S. PATENT DOCUMENTS

| | | | |
|---|---|---|---|
| 3,947,465 | 3/1976 | Coll | 548/110 |
| 4,360,686 | 11/1982 | Wang | 548/110 |
| 4,412,078 | 10/1983 | Berger | 548/110 |
| 4,465,836 | 8/1984 | Buschhaus | 548/110 |

FOREIGN PATENT DOCUMENTS 51-75070  6/1976  Japan .................. 548/110

OTHER PUBLICATIONS

Casper, Peter, Chpt. 9, pp. 335-383, "Silyenes"; *Reactive Intermediates*; edited by Jones: Wiley & Sons, 1981.
Pierce—Silyation of Organic Compounds; 1968, Pierce Chem. Co., Rockford, Illnois.
Corriu et al— "N,N—bis(silyl)enamines, etc.", (1982), Tetrahedron Letters, vol. 23, pp. 3257-3260.
Corriu et al: Tetrahedron Letters 23(32), pp. 3257-3260, 1982, N,N-bis(silyl)enamines as Protected Vinylamines.
Klebe, "Silyation in Organic Research", Advances in Organic Chemistry, Methods and Results, vol. 8, (Wiley—Interscience, 1972), pp. 146-147, 154-155.
CA 87:117773s, Iyoda et al; Silicone-Containing Pyrolidene compounds (1977).
CA 87:68490m, Iyoda et al; Silicon-Containing Pyrolidenes (1977).
CA 101:72814u, Burger et al; Pyrolysis of Trimethylsilyl N-chlorobenzimidates (1984).
Noyori, R.; Yokoyama, K.; Sakata, J.: Kuwajima, I.; Nakamura, E.; Shimizu, M., *J. Am. Chem. Soc.*, 99, 1265-67 (1977).
Noyori, R.; Nishida, I.; Sakata, J., *J. Am. Chem. Soc.*, 103, 2106-08 (1981).
R. Yocum & E. B. Nyquist (eds.), *Functional Monomers*, vol. two, Marcel Dekker, Inc. (1974) p. 65.

*Primary Examiner*—Glennon H. Hollrah
*Assistant Examiner*—D. L. Dinner

[57] ABSTRACT

The invention is a process for the preparation of a N- or S-1,2-ethylenically unsaturated organic compound which comprises
 (a) contacting a N- or S-silylated organic compound with an aldehyde, wherein the aldehyde has a hydrogen atom bonded to the carbon adjacent to the carbonyl moiety, at elevated temperatures under conditions such that a N- or S-1-siloxyalkyl-substituted organic compound is prepared; and
 (b) pyrolyzing the N- or S-1-siloxyalkyl-substituted organic compound under conditions such that the siloxy moiety is elminated to prepare a N- or S-1,2-ethylenically unsaturated compound.

14 Claims, No Drawings

PREPARATION OF N- AND S-1,2-ETHYLENICALLY UNSATURATED ORGANIC COMPOUNDS

BACKGROUND OF THE INVENTION

This invention relates to a process for the preparation of N- and S-1,2-ethylenically unsaturated organic compounds. The compounds prepared by the process of this invention are useful in the preparation of polymeric compositions, for example, plastic polymeric compositions.

It is often desirable to impart to polymeric compositions certain specific properties. This is done by incorporating into the poltmeric composition a monomer which has or imparts such properties to the polymeric composition. In polymeric compositions which are prepared by polymerizing compounds with 1,2-ethylenically unsaturated moieties, it is desirable to have compounds with the desired properties which contain 1,2-ethylenically unsaturated moieties.

Many processes which prepare compounds substituted with 1,2-ethylenically unsaturated moieties result in low yields, undesirable by-products, for instance salt by-products and by-products which are deleterious to the environment, or involve complicated synthesis schemes. What is needed in the art is a process for substituting nitrogen- and sulfur-containing compounds with 1,2-ethylenically unsaturated moieties on the nitrogen and sulfur atoms, in which good yields are achieved and which do not result in the preparation of undesirable by-products.

SUMMARY OF THE INVENTION

The invention is a process for the preparation of a N- or S-1,2-ethylenically unsaturated organic compound which comprises
(a) contacting a N- or S-silylated organic compound with an aldehyde, wherein the aldehyde has a hydrogen atom bonded to the carbon adjacent to the carbonyl moiety, at elevated temperatures under conditions such that a N- or S-1-siloxyalkyl-substituted organic compound is prepared; and
(b) pyrolyzing the N- or S-1-siloxyalkyl-substituted organic compound under conditions such that the siloxy moiety is eliminated to prepare a N- or S-1,2-ethylenically unsaturated compound.

DETAILED DESCRIPTION OF THE INVENTION

The starting reactants for this reaction are the reaction products of a silylation agent and an organic compound which contains a nitrogen or sulfur atom wherein the reaction product has a nitrogen or sulfur atom which is silylated. Compounds which are useful in preparing the reaction product of the silylation agent and the nitrogenor sulfur-containing organic compound include amides, cyclic amides, imides, hydantoins, uracils, amines, sulfonamides, saccharin, ureas, cyclic ureas, oxazolidinones, isooxazolidinones, isatoic anhydride, and mercaptans.

Amides useful in this invention include those corresponding to the formula

wherein $R^1$ is hydrogen or a $C_{1\text{-}20}$ hydrocarbyl group.

Cyclic amides useful in this invention include those which correspond to the formula

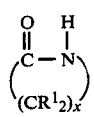

wherein X is between about 2 and 4.

Cyclic imides useful in this invention include those which correspond to the formula

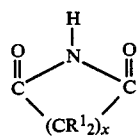

wherein x is between about 2 and 4.

Hydantoins useful in this process include those which correspond to the formula

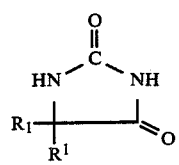

wherein $R^1$ is as defined hereinbefore.

Uracil refers herein to compounds which correspond to the formula

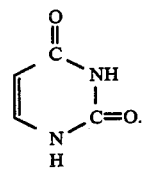

Amines useful in this process include those which correspond to the formula

wherein $R^1$ is as defined hereinbefore; a is the integer 1 or 2; and b is the integer 1 or 2; with the proviso that the sum of a and b must equal 3.

Sulfonamides useful in this process include those which correspond to the formula

wherein $R^1$ is as defined hereinbefore; c is the integer 0 or 1; and d is the integer 1 or 2; with the proviso that the sum of c and d must equal 2.

Saccharin refers herein to the compound which corresponds to the formula

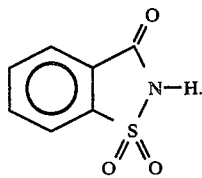

Ureas useful in this process include those which correspond to the formula

wherein $R^1$ is as defined hereinbefore.

Cyclic urea refers herein to those compounds which correspond to the formula

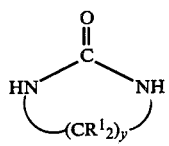

wherein y is an integer between about 2 and 4.

Isooxazolidinone refers herein to those compounds which correspond to the formula

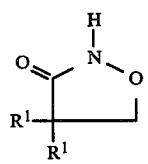

wherein $R^1$ is as defined hereinbefore.

Isatoic anydride refers herein to the compound which corresponds to the formula

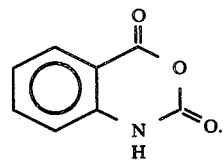

Oxazolidinones useful in this invention include those which correspond to the formula

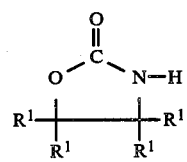

wherein $R^1$ is as defined hereinbefore.

Mercaptans useful in this invention include those which correspond to the formula

wherein $R^1$ is as defined hereinbefore.

Preferred reactants are the nitrogen-containing organic compounds. More preferred are the heterocyclic nitrogen-containing organic compounds, which include cyclic amides, cyclic imides, hydantoins, uracils, saccharin, cyclic ureas, isooxazolidinones, isatoic anhydride and oxazolidinones. Even more preferred are the cyclic amides, cyclic ureas, oxazolidinones and isooxazolidinones, with oxazolidinoness being most preferred.

Nonlimiting examples of N- or S-silylated organic compounds include the following: N-silylated amides which correspond to the formula

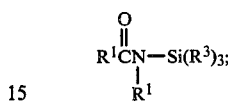

N-silylated cyclic amides which correspond to the formula

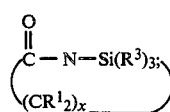

N-silylated imides which correspond to the formula

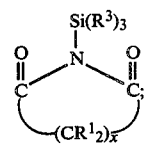

N-silylated hydantoins which correspond to the formula

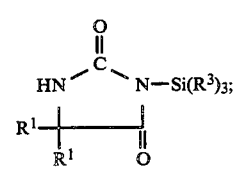

N-silylated uracil which corresponds to the formula

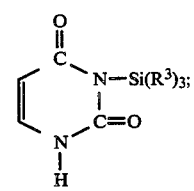

N-silylated amines which correspond to the formula

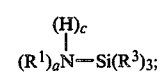

N-silylated sulfonamides which correspond to the formula

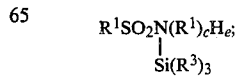

N-silylated saccharin which corresponds to the formula

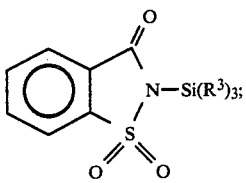

N-silylated ureas which correspond to the formula

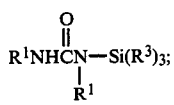

N-silylated cyclic ureas which correspond to the formula

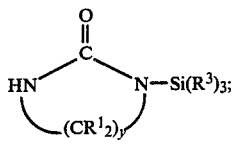

N-silylated isooxazolidinones which correspond to the formula

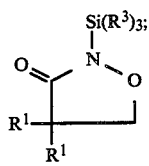

N-silylated isatoic anhydride which corresponds to the formula

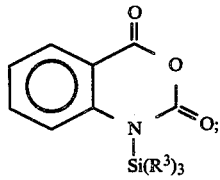

N-silylated oxazolidinones which correspond to the formula

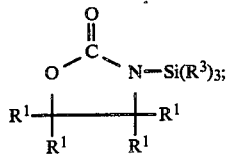

and
S-silylated mercaptans which correspond to the formula $R^1S-Si(R^3)_3$.

The preferred silylated organic compounds are the N-silylated organic compounds. These compounds are the reaction product of a silylation agent and an amide, a cyclic amide, an imide, a hydantoin, uracil, an amine, a sulfonamide, saccharin, a urea, a cyclic urea, an isooxazolidinone, isatoic anhydride, and an oxazolidinone.

More preferred silylated organic compounds are those which are the reaction product of a silylation agent and a nitrogen-containing heterocyclic compound. Even more preferred are the silylated organic compounds which are the reaction product of a silylation agent and cyclic amides, cyclic ureas, oxazolicinones, or isooxazolidinones.

In a most preferred embodiment, the silylated organic compound is the reaction product of a silylation agent and an oxazolidinone.

In the first step the silylated organic compound is contacted with an aldehyde.

Aldehydes useful in this process include any aldehyde which has a hydrogen atom on the carbon adjacent to the carbonyl moiety. Preferred aldehydes include those which correspond to the formula

wherein $R^2$ is hydrogen or a $C_{1-20}$ hydrocarbyl group.

Generally, the product of the first step of the hereinbefore-described process is a N- or S-1-siloxyalkyl-substituted organic compound. Examples of N- or S-1-siloxyalkyl-substituted organic compounds include N-1-siloxyalkylamides, N-1-siloxyalkyl cyclic amides, N-1siloxyalkylimides, N-1-siloxyalkyl hydantoins, N-1-siloxyalkyl uracil, N-1-siloxyalkylamines, N-1-siloxyalkyl sulfonamide, N-1-siloxyalkyl saccharin, N-1-siloxyalkyl ureas, N-1-siloxyalkyl cyclic ureas, N-1-siloxyalkyl isooxazolidinones, N-1-siloxyalkyl isatoic anhydride, N-1-siloxyalkyl oxazolidinones, and S-1-siloxyalkyl mercaptans. Preferred products are N-1-siloxyalkyl-substituted organic compounds. More preferred N-1-siloxyalkyl-substituted organic compounds include the N-1-siloxyalkyl cyclic amides, N-1-siloxyalkyl cyclic ureas, N-1-isooxazolidinones and N-1-siloxyalkyl oxazolidinones. In one most preferred embodiment, the product is a N-1-siloxyalkyl oxazolidinone.

Nonlimiting examples of N- or S-2-siloxyalkyl-substituted organic compounds include the following: N-1-siloxyalkyl-substituted amides correspond to the formula

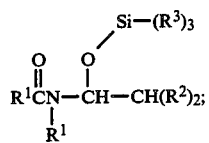

N-1-siloxyalkyl cyclic amides correspond to the formula

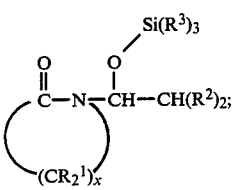

N-1-siloxyalkylimides correspond to the formula

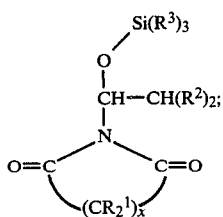

N-1-siloxyalkyl hydantoins correspond to the formula

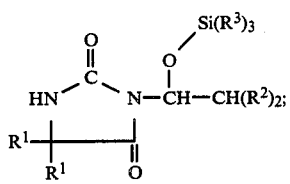

N-1-siloxyalkyl uracil corresponds to the formula

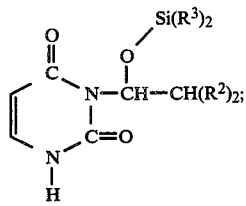

N-1-siloxyalkylamines correspond to the formula

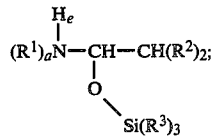

N-1-siloxyalkyl sulfonamides correspond to the formula

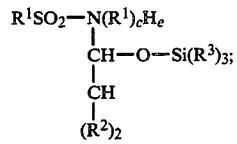

N-1-siloxyalky saccharin corresponds to the formula

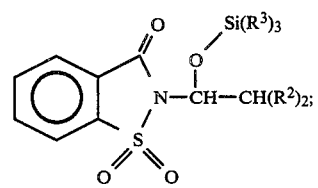

N-1-siloxyalkyl ureas correspond to the formula

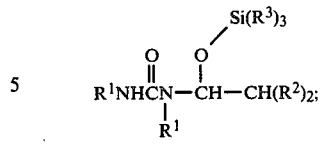

N-1-siloxyalkyl cyclic ureas correspond to the formula

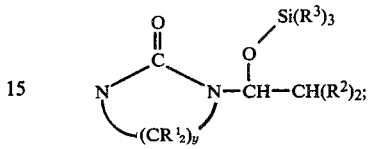

N-1-siloxyalkyl isooxazolidinones correspond to the formula

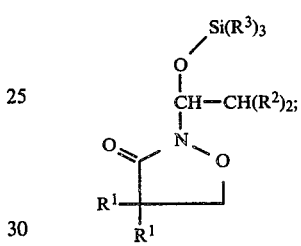

N-1-siloxyalkyl isatoic anhydride corresponds to the formula

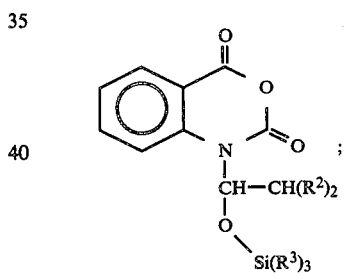

N-1-siloxyalkyl oxazolidinones correspond to the formula

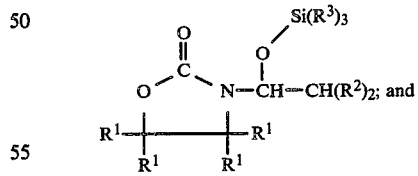

S-1-siloxyalkyl mercaptans correspond to the formula

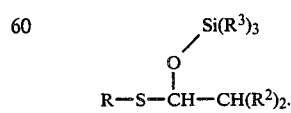

In the second step of this process, the siloxyalkyl-substituted organic compounds are pyrolyzed to prepare the products of this process which are N- or S-1,2-ethylenically unsaturated organic compounds. Examples of such compounds include N-1,2ethylenically unsaturated amides, N-1,2-ethylenically unsaturated cyclic amides, N-1,2-ethylenically unsaturated imides, N-1,2-ethylenically unsaturated hydantoins, N-1,2-ethylenically unsaturated uracils, N-1,2-ethylenically unsaturated amines, N-1,2-ethylenically unsaturated sulfonamides, N-1,2-ethylenically unsaturated saccharin, N-1,2-ethylenically unsaturated ures, N-1,2-ethylenically unsaturated cyclic ureas, N-1,2-ethylenically unsaturated isooxazolidinones, N-1,2-ethylenically unsaturated isatoic anhydrides, N-1,2-ethylenically unsaturated oxazolidinones, and S-1,2-ethylenically unsaturated mercaptans. The preferred 1,2-ethylenically unsaturated compounds are N-1,2-ethylenically unsaturated organic compounds. More preferred N-1,2-ethylenically unsaturated organic compounds are the N-1,2-ethylenically unsaturated cyclic amides, N-1,2-ethylenically unsaturated cyclic ureas, N-1,2-ethylenically unsatureated oxazolidinones and the N-1,2-ethylenically unsaturated isooxazolidinones with N-1,2-ethylenically unsaturated oxazolidinones being most preferred.

Nonlimiting illustrations of the N- or S-1,2-ethylenically unsaturated organic compounds include the following: N-1,2ethylenically unsaturated amides which correspond to the formula

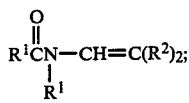

N-1,2-ethylenically unsaturated cyclic amides which correspond to the formula

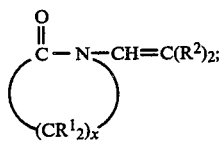

N-1,2-ethylenically unsaturated imides which correspond to the formula

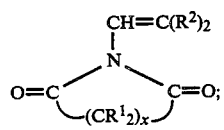

N-1,2-ethylenically unsaturated hydantoins which correspond to the formula

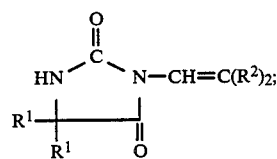

N-1,2-ethylenically unsaturated uracil which corresponds to the formula

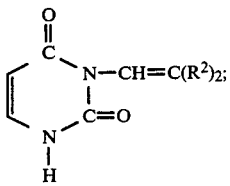

N-1,2-ethylenically unsaturated amines which correspond to the formula

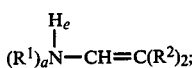

N-1,2-ethylenically unsaturated sulfonamides which correspond to the formula

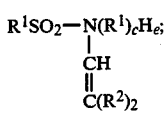

N-1,2-ethylenically unsaturated saccharin which corrresponds to the formula

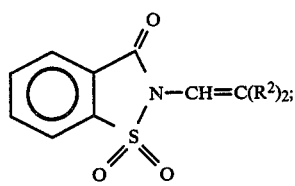

N-1,2-ethylenically unsaturated ureas which correspond to the formula

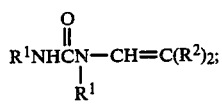

N-1,2-ethylenically unsaturated cyclic ureas which correspond to the formula

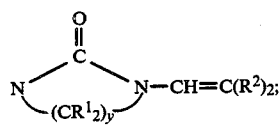

N-1,2-ethylenically unsaturated isooxazolidinone which corresponds to the formula

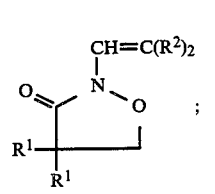

N-1,2-ethylenically unsaturated isatoic anhydride which corresponds to the formula

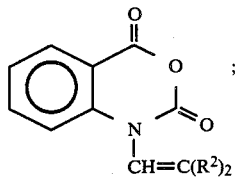

N-1,2-ethylenically unsaturated oxazolidinones which correspond to the formula

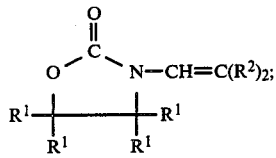

and S-1,2-ethylenically unsaturated mercaptans which correspond to the formula $$RS-CH=C(R^2)_2;$$

wherein $R^1$, $R^2$, a, b, c, d, and e are as defined hereinbefore.

In the hereinbefore-described formulas, $R^1$ is preferably $C_{1-20}$ alkyl, $C_{1-20}$ alkenyl, $C_{7-20}$ alkaryl or $C_{6-20}$ aryl; more preferably $C_{1-10}$ alkyl, $C_{1-10}$ alkenyl, phenyl, or benzyl. $R^1$ is most preferably $C_{1-5}$ alkyl, $C_{1-5}$ alkenyl, phenyl, or benzyl.

$R^2$ is preferably a $C_{1-20}$ *alkyl group*, $C_{1-20}$ alkenyl group or a $C_{1-20}$ alkaryl group. $R^2$ is more preferably a $C_{1-10}$ alkyl $C_{1-10}$ alkenyl, or $C_{7-10}$ alkaryl group. $R^2$ is most preferably $C_{1-4}$ alkyl, $C_{1-4}$ alkenyl, or benzyl.

$C_{1-20}$ hydrocarbyl means herein an organic radical containing between one and twenty carbon atoms to which are bonded hydrogen atoms. Included are the following groups: $C_{1-20}$ alkyl, $C_{1-20}$ alkenyl, $C_{1-20}$ alkynyl, $C_{3-20}$ cycloalkyl, $C_{3-20}$ cycloalkenyl, $C_{6-20}$ aryl, $C_{7-20}$ alkaryl or $C_{7-20}$ aralkyl.

The term aryl refers herein to biaryl, phenyl, naphthyl, phenanthranyl and anthranyl. Alkaryl refers herein to an alkyl-, alkenyl- or alkynyl-substituted aryl substituent wherein aryl is as defined hereinbefore. Aralkyl means herein an alkyl, alkenyl or alkynyl substituent substituted with an aryl group, wherein aryl is as defined hereinbefore.

$C_{3-20}$ cycloalkyl refers to an alkyl group containing one, two, three or more cyclic rings. $C_{3-20}$ cycloalkenyl refers to mono-, di- and polycyclic groups containing one or more double bonds. $C_{3-20}$ cycloalkenyl also refers to the cycloalkenyl groups wherein two or more double bonds are present.

The process of this invention can be illustrated by the following equation which demonstrates one of the preferred embodiments.

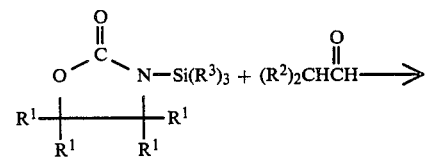

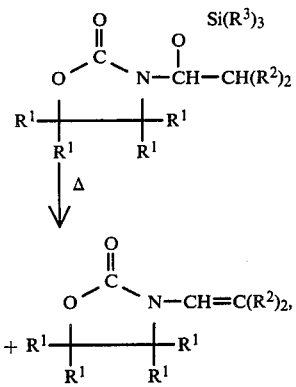

wherein $R^1$, $R^2$ and $R^3$ are as defined hereinbefore.

In the first step, step (a), an aldehyde and a N- or S-silylated organic compound are contacted at elevated temperatures under conditions such that a N-or S-1-siloxyalkyl-substituted organic compound is prepared. The aldehyde and S-silylated organic compound are contacted in a mole ratio of between about 1.5:1.0 and 1.0:1.0, more preferably between about 1.2:1.0 and 1.0:1.0, most preferably about 1.0:1.0. In those embodiments wherein the aldehyde is volatile, the use of a 10 to 50 percent excess of aldehyde is desirable. This contacting is preferably done neat, in other words in the absence of a solvent. If desired, inert organic solvents which do not contain active hydrogen atoms can be used, for example, chlorinated aliphatic hydrocarbons, chlorinated aromatic hydrocarbons, aromatic hydrocarbons and aliphatic hydrocarbons. Preferred solvents are the aromatic hydrocarbons, with toluene being the most preferred aromatic hydrocarbon.

It is preferable to do this contacting at the reflux temperature of the reaction mixture. Preferably the temperature for this reaction is between about 80° C. and 200° C., with between about 100° C. and 150° C. being most preferred.

No catalyst is necessary for this reaction to take place. Optionally, catalysts such as ammonium salts or phosphonium salts may be used as catalysts in this reaction. Generally, a sufficient amount of such catalyst to catalyze the reaction is suitable. Preferably between about 0.01 and 5 weight percent of the catalyst is used, with between about 1 and 2 weight percent being most preferred.

This process can be done at atmospheric and superatmospheric pressures. It is preferable to run the reaction at superatmospheric pressures because of the volatility of the aldehyde. Preferred pressures are between about 100 psi (689 kPa) and 500 psi (3447 kPa), with between about 200 psi (1378 kPa) and 300 psi (2068 kPa) being most preferred.

In one preferred embodiment, the aldehyde is added dropwise to the reaction mixture, so as to prevent volatilization of the aldehyde before it reacts with the N- or S-silylated organic compound.

In the second step, step (b), the N- or S-1-siloxyalkyl-substituted organic compound is pyrolyzed to prepare a N- or S-1,2-ethylenically unsaturated organic compound. This pyrolysis can take place at any temperature at which the siloxy moiety is removed from the starting compound so as to prepare the ethylenically unsaturated moiety. Preferable temperatures are between about 150° C. and 500° C., with between about 250° C. and 300° C. being most preferred.

No catalyst is necessary for this reaction step, although optional catalysts may be used which include acids and bases. Acid catalysts are the preferred catalysts. When a catalyst is used, it is preferable that the catalyst be placed on a support.

A preferred mode of pyrolysis involves the use of a hot tube reactor packed with a suitable packing. Suitable packings are those which are stable at pyrolysis conditions and inert to the reactant. Among suitable packings are glass beads, stainless steel helices and Carborundum ® beads. The purpose of the packing is to prevent the reactants from passing through the hot tube too fast.

It is desirable to pass an inert gas through the hot tube during the reaction so as to push the vaporized reactants and products through the hot tube.

In some cases, complete pyrolysis does not occur in one pass of the reactants through the hot tube. Thus, is may be advantageous to pass the reactants through the hot tube two or more times until an acceptable conversion is reached. In a situation where a catalyst is used in a hot tube reactor, the catalyst can be supported by coating the packing with a catalyst.

A suitable pressure for this reaction step is that pressure at which the reaction occurs. Preferable pressures are between about 10 (1.333 kPa) and 760 (101.32 kPa) mm Hg, more preferably between about 50 (6.66 kPa) and 500 (66.660 kPa) mm Hg, with between about 300 (40.00 kPa) and 400 (533.288 kPa) mm Hg being most preferred. Generally, any pyrolysis time at which the reaction occurs is suitable, preferably between about 1 and 120 seconds, more preferably between 1 and 10 seconds.

The product may be recovered by any means known in the art. A particularly suitable means of recovery of the desired product is distillation.

The N- or S-silylated organic compound is the reaction product of a nitrogen- or sulfur-containing organic compound and a silylation agent. A silylation agent herein refers to any silicon-containing compound which will react with any organic compound which contains a nitrogen or sulfur atom containing a hydrogen atom bonded thereto. Suitable silylation agents include those which correspond to the formula

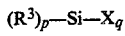

wherein $R^3$ is as defined hereinbefore, X is a halogen, p is the integer 2 or 3 and q is the integer 1 or 2, with the proviso that p+q must equal 4. Examples of silylation agents include trimethylchlorosilane, dimethyltertiary butylchlorosilane, dimethyldichlorosilane and diphenyldichlorosilane.

In general, the sulfur- or nitrogen-containing organic compound is contacted with the silylation agent in the presence of a tertiary organic base, an acid acceptor. This can be done at a temperature of between about 20° C. and 40° C. Examples of suitable tertiary bases include triethylamine, N-ethylpiperadine, quinoline and picolines. This process is usually done in an organic solvent, both protides and aprotides, of low dielectric constant are suitable. Examples of preferable solvents include the halogenated aliphatic hydrocarbons. The silylation of organic compounds is demonstrated by U.S. Pat. No. 3,947,465, incorporated herein by reference.

SPECIFIC EMBODIMENT

The following example is included for illustrative purposes only, and does not limit the scope of the claims or the invention. All parts and percentages are by weight unless otherwise specified.

EXAMPLE

Trimethylchlorosilane (13.25 ml, 0.1 mole) is added dropwise to a refluxing mixture of 8.7 g (0.1 mole) of 2-oxazolidinone, 13.85 ml of triethylamine and dry toluene (350 ml) and the whole is heated for a further 3 hours under refluxing with stirring. After cooling, the precipitated trimethylammonium chloride is filtered off and the toluene is removed under reduced pressure. After removal of the toluene, 4.4 g (excess) of acetaldehyde is added dropwise at 150° C. to the crude silylated 2-oxazolidinone and the whole is kept at 150° C. with stirring for a further 2 hours. After reaction, the condenser is replaced with a distillation head and N-1-siloxyethyl-2-oxazolidinone is isolated by distillation, in an 80 percent yield.

The N-1-siloxyethyl-2-oxazolidinone (10.2 g, 0.5 mole) is passed through a 12-in by 1-in quartz tube filled with stainless steel rings. The tube is preheated to 300° C. and a continuous nitrogen flow prevents the buildup of vapor in the head space. A dark red mixture is collected from the dry ice-cooled receiver. Fractionation of the mixture gives 3.2 g of N-vinyl-2-oxazolidinone, a yield of 70 percent based on 90 percent conversion of the N-siloxyethyl-2-oxazolidinone.

What is claimed is:

1. A process for the preparation of a compound selected from the group consisting of N- and S-1,2-ethylenically unsaturated organic compounds which comprises
   (a) contacting a compound selected from the group consisting of N- and S-silylated organic compounds with an aldehyde, wherein the aldehyde has a hydrogen atom bonded to the carbon adjacent to the carbonyl moiety, at elevated temperatures under conditions such that a compound selected from the group consisting of N- and S-siloxyalkyl-substituted organic compounds is prepared; and
   (b) pyrolyzing the compound selected from the group consisting of N- and S-1-siloxyalkyl-substituted organic compounds under conditions such that the siloxy moiety is eliminated to prepare the compound selected from the group consisting of N- and S-1,2-ethylenically unsaturated compounds.

2. The process of claim 1 wherein the aldehyde is reacted with a N-silylated organic compound.

3. The process of claim 2 wherein the N-silylated organic compound is the reaction product of a silylation agent and a nitrogen-containing heterocyclic compound.

4. The process of claim 3 wherein the nitrogen-containing heterocyclic compound is a compound selected from the group consisting of a cyclic amide, a cyclic urea, an oxazolidinone and an isooxazolidinone.

5. The process of claim 4 wherein the nitrogen-containing heterocyclic compound is oxazolidinone.

6. The process of claim 1 wherein the aldehyde corresponds to the formula

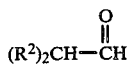

wherein $R^2$ is a $C_{1-20}$ hydrocarbyl group with the proviso that the carbon adjacent to the carbonyl moiety has a hydrogen atom bonded to it.

7. The process of claim 6 wherein the aldehyde and the compound selected from the group consisting of N- and S-silylated organic compounds are contacted at reflux of the reaction mixture.

8. The process of claim 7 wherein the reflux temperature is between about 100° C. and 150° C.

9. The process of claim 7 wherein the contacting of the aldehyde and the compound selected from the group consisting of N- and S-silylated organic compounds is done in an inert organic solvent.

10. The process of claim 7 wherein the contacting of the aldehyde and the compound selected from the group consisting of N- and S-silylated organic compounds is done in the presence of a catalytic compound of a catalyst which is a compound selected from the group consisting of phosphonium and ammonium salt.

11. The process of claim 1 wherein the pyrolysis temperature is between 250° C. and 500° C.

12. The process of claim 11 wherein the compound selected from the group consisting of N- and S-1-siloxyalkyl organic compounds are pyrolyzed in the presence of an acid or a base catalyst.

13. The process of claim 12 wherein the catalyst is an acid.

14. The process of claim 13 wherein the pressure is between 50 and 500 mm Hg.

* * * * *